United States Patent
Iwamoto et al.

[11] Patent Number: 6,162,337
[45] Date of Patent: Dec. 19, 2000

[54] LARGE AREA ION CONCENTRATION MEASURING ELECTRODE AND METHOD OF MANUFACTURING SAME

[75] Inventors: Yasukazu Iwamoto; Shinji Takeichi, both of Miyanohigashi-machi, Japan

[73] Assignee: Horiba, Ltd., Kyoto, Japan

[21] Appl. No.: 09/262,793

[22] Filed: Mar. 4, 1999

[30] Foreign Application Priority Data

Mar. 7, 1998 [JP] Japan .................... 10-073379

[51] Int. Cl.[7] .................. G01N 27/26; G01N 27/416
[52] U.S. Cl. .................. 204/409; 204/416; 204/420; 156/281; 156/296
[58] Field of Search .................. 204/409, 416, 204/420, 433; 205/787.5; 156/281, 296, 310, 321

[56] References Cited

U.S. PATENT DOCUMENTS

| | | | |
|---|---|---|---|
| 4,519,890 | 5/1985 | Uematsu et al. | 204/409 |
| 4,556,473 | 12/1985 | Kohno et al. | 204/409 |
| 4,935,117 | 6/1990 | Uematsu et al. | 204/411 |
| 5,639,368 | 5/1985 | Davis et al. | 204/409 |

*Primary Examiner*—Robert J. Warden, Sr.
*Assistant Examiner*—Kaj K. Olsen
*Attorney, Agent, or Firm*—Price and Gess

[57] ABSTRACT

An ion concentration measuring electrode unit includes a body member having a plurality of capillary tubes extending through the body member to provide a plurality of passageways for a sample fluid to be tested. The gaps between the hollow tubes are sealed to maintain an internal solution complimentary to the ion to be measured. An internal electrode is immersed within the internal solution whereby a large internal surface area is provided to enable a reduced impedance in measurement of a sample fluid. An ion concentration meter assembly is thereby provided when combined with a sample flow conduit directing fluid through the body member with a liquid junction connected to the conduit and to a reference electrode unit whereby outputs of the internal electrode and a reference electrode can be used to measure an ion concentration.

20 Claims, 5 Drawing Sheets

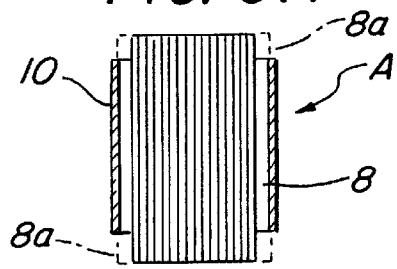
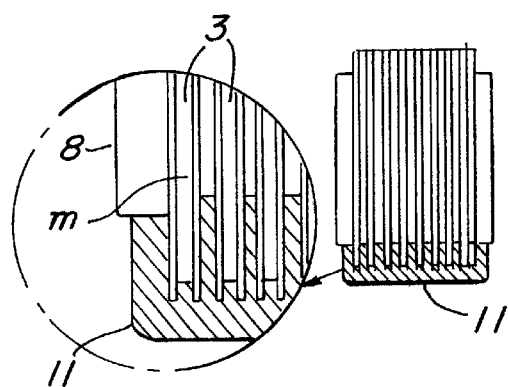
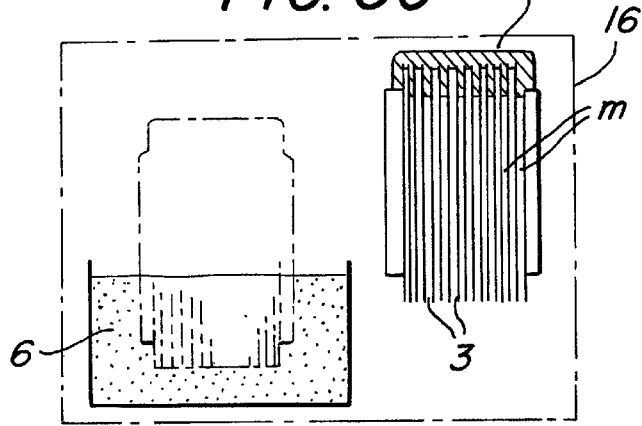
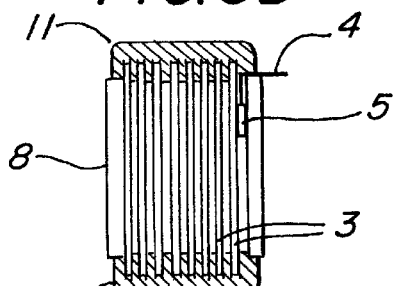
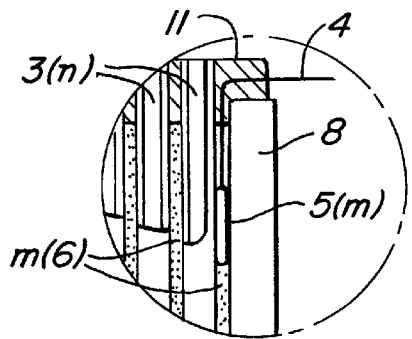
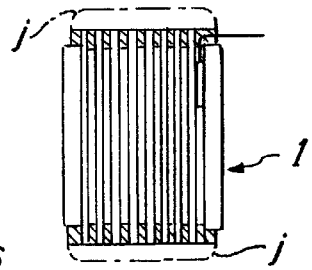
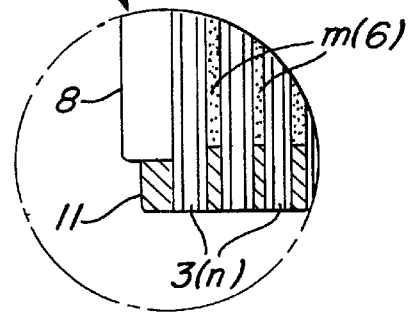

LARGE AREA ION CONCENTRATION MEASURING ELECTRODE AND METHOD OF MANUFACTURING SAME

BACKGROUND OF THE INVENTION

1. Field of the Invention

The present invention relates to an ion concentration measuring electrode that is capable of being used to measure pH and various ions and a method of manufacturing an ion concentration measuring electrode, and more particularly, to a low impedance ion concentration measuring electrode that can be readily adapted for flow-through measurements.

2. Description of Related Art

The prior art is aware of numerous different procedures and apparatus for measurement of pH and ion concentrations. This technical field has been very active for a considerable period of time and both laboratory and industrial instruments have been successfully utilized. As an illustrative example, FIG. 5 discloses a schematic of a pH meter that comprises a glass electrode a (ion concentration measuring electrode) and a reference electrode b. A glass internal electrode c is mounted within a housing and emerged in a glass electrode internal solution d. The tip of the housing is an electrode response section e. A reference electrode internal electrode f is mounted in the housing of the reference electrode b and it also contains a reference electrode internal solution h. At the tip of the housing is a liquid junction i. A comparison of the outputs of the respective electrodes a and b provide a voltage reading indicative of the pH measurement.

The electrode response section e can be made of a spherical thin film glass in the range of thickness of 100 to 150 microns. Since the surface area which provides the liquid contact is relatively small and narrow, a very large impedance (usually in the range of 100 Mohms) is experienced. Therefore, a high input insulated circuit of $10^{12}$ ohms, or more, is usually required for measuring the electromotive force, with the resulting complications in the electric circuit.

While it may be assumed that the pH response performance of such an electrode response section e could be enhanced by further reducing the thickness of the glass film, which is in contact with the liquid sample, there is a limitation in terms of strength and processing procedures, and accordingly, a practical limitation is a glass film thickness of 100 to 150 microns which makes it extremely difficult to produce thinner products that could be commercially utilized.

Thus, the prior art has experienced certain limitations as a result of the conventional designs of the electrode response sections in pH meters and various ionic measurement instruments.

SUMMARY OF THE INVENTION

The present invention provides an ion concentration measuring electrode unit that has a body member with a bundle of hollow capillary tubes extending through the body member. The body member can be a glass tube which is packed with the parallel aligned capillary tubes, heated to 700° C., and then subsequently drawn through a series of dies to provide a composite intermediate product of a reduced dimension. The resulting internal diameter of the capillary tubes is approximately in the range of 10 to 100 microns. The capillary tubes can be formed from glass $SiO_2$—$Li_2O$. The resulting wall thickness of the hollow capillary tubes will be about 10 microns. The interior passageway of the capillary tubes can permit a sample fluid to flow through it. An internal solution complimentary to the ions being measured is positioned in the gaps between the tubes to surround and contact the exterior surfaces of the capillary tubes. The internal solution can be a gel, slurry or a liquid that can be drawn by a vacuum into the gaps between the respective capillary tubes. An internal electrode is immersed within the internal solution to provide an output measurement of the sample fluid. The particular construction increases the effective surface area so that a large internal surface area is provided by the plurality of passageways for interfacing with the internal solution on the exterior surfaces of the hollow capillary tubes to thereby enable a reduced impedance in measuring a sample fluid.

An ion concentration meter assembly, such as a pH meter can be provided with a sample flow conduit that mounts a body member having the plurality of bundled capillary tubes. An internal electrode is immersed within an internal solution that is surrounding the exterior surfaces of the capillary tubes to provide a larger surface area to enable a reduced impedance in measuring the sample flow. A liquid junction can be connected to the sample flow conduit and a reference electrode unit is connected to the liquid junction and has a reference electrode mounted in a reference solution. The output signal voltage can be used, for example, by a microprocessor based circuit to calculate a measurement of the ion concentration, such as pH, in the sample fluid.

In the manufacturing of an ion concentration measuring electrode unit, a plurality of glass capillary tubes are bundled together and mounted within an outer glass housing. This composite structure is then heated to a temperature of 650° C.–700° C. and redrawn through a series of dies, so as to reduce the capillary tubes to a wall thickness of about 10 microns, with a passageway diameter in the approximate range of 10 to 100 microns. This intermediate structure can then be diced to the specific length desired. The sides of the composite structure can be masked with an acid resistant heat shrink tube and the ends of the outside glass tube can then be dissolved to expose the end sides of the capillary tubes. One end of the capillary tubes can be molded in a thermoplastic resin, whereby the resin will penetrate further up the small gaps between the exterior surfaces of the capillary tubes than it will within the passageways. The composite structure can then be placed into a vacuum environment and inserted into an internal solution of either a gel, slurry or liquid form so that the internal solution is positioned in the gaps between the exterior surfaces of the capillary tubes. An internal electrode is inserted with an appropriate lead wire into a gap and the other end of the capillary tube is sealed with a thermoplastic resin. Subsequently, the sealing material is removed to expose the passageways of the capillary tubes while leaving the sealing material in place to hold the internal solution. As a result, a large internal surface area is provided by the passageways for interfacing with the internal solution on the exterior surfaces of the capillary tubes to enable a reduced impedance in measurement of the sample fluid.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may be best understood by reference to the following description, taken in connection with the accompanying drawings.

FIGS. 3A–3G schematically show the process forming steps of making an ion concentration measuring electrode;

FIG. 3A is a cross sectional view of the composite glass tube and bundled capillary tubes with the ends of the outer glass tube dissolved to expose the capillary tubes;

FIG. 3B discloses a cross sectional view of the capillary tubes covered by a resin material with an enlarged partial cross sectional view;

FIG. 3C is a schematic illustration of a vacuum injection procedure for inserting an internal solution;

FIG. 3D is a composite cross sectional view disclosing the other end of the composite structure sealed by resin;

FIGS. 3E, F and G disclose respective steps of cutting off the resin molded portion to maintain the seal for the internal solution while exposing the passageways in the capillary tubes;

DETAILED DESCRIPTION OF THE PREFERRED EMBODIMENTS

The following description is provided to enable any person skilled in the art to make and use the invention and sets forth the best modes contemplated by the inventors of carrying out their invention. The present invention has been designed specifically to provide a large area ion concentration measuring electrode, a flow through ion concentration measuring meter, and a method of manufacturing an ion concentration measuring electrode.

Figure 1:
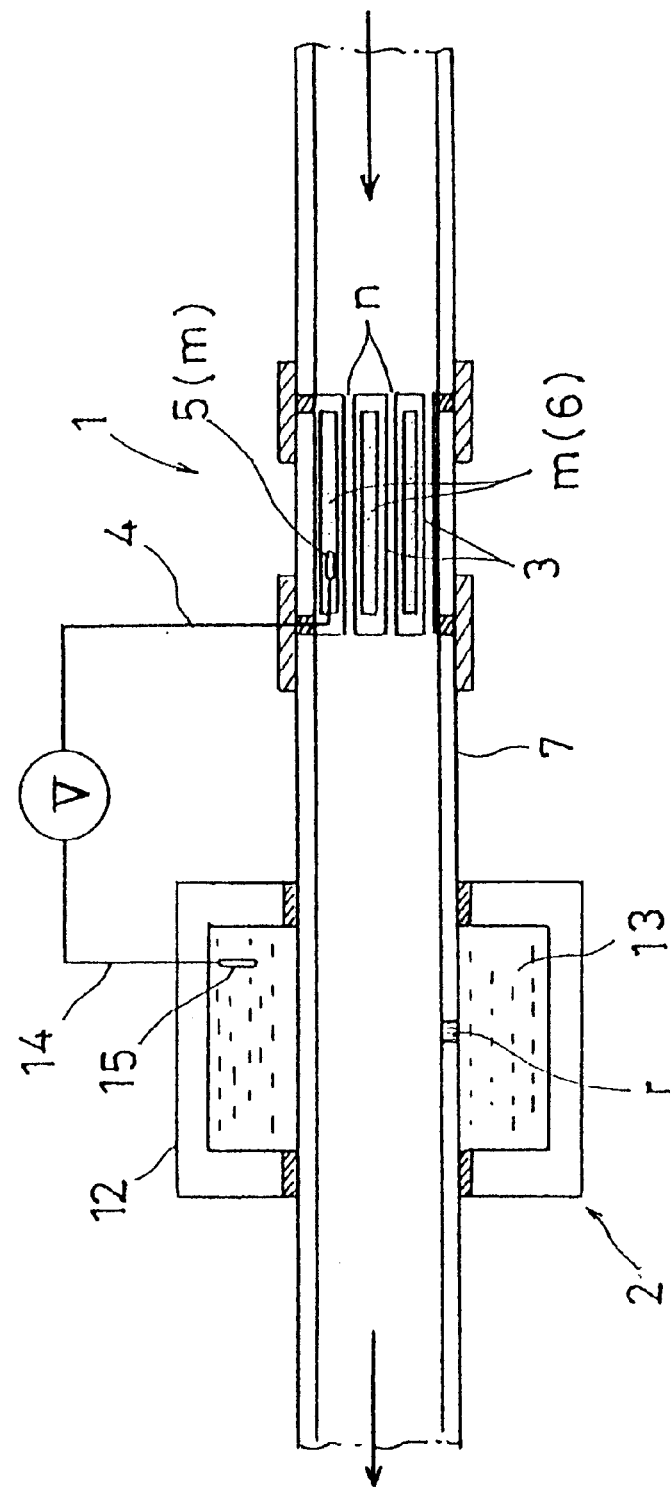
FIG. 1 is a schematic cross sectional view of a flow through pH meter of the present invention.

Referring to FIG. 1, a flow-through ion concentration measuring meter unit of the present invention is disclosed. This measuring unit incorporates an ion concentration measuring electrode as the glass electrode 1 with the reference electrode 2 appended downstream of the glass electrode 1. A sample fluid can flow through passageways in a plurality of capillary tubes 3 that have been bundled together. An internal electrode, (Ag/AgCl) 5, can be connected to a lead wire 4 and can be positioned between the internal gaps between the exterior surfaces of the capillary tubes 3. These gaps between the tubes are sealed so that they can be liquid tight to maintain an internal solution such as KCl which has been injected into the gaps m. A flow conduit 7 made, for example, of quartz can be used for permitting the sample to flow through the ion concentration measuring electrode 1.

Figure 2A:
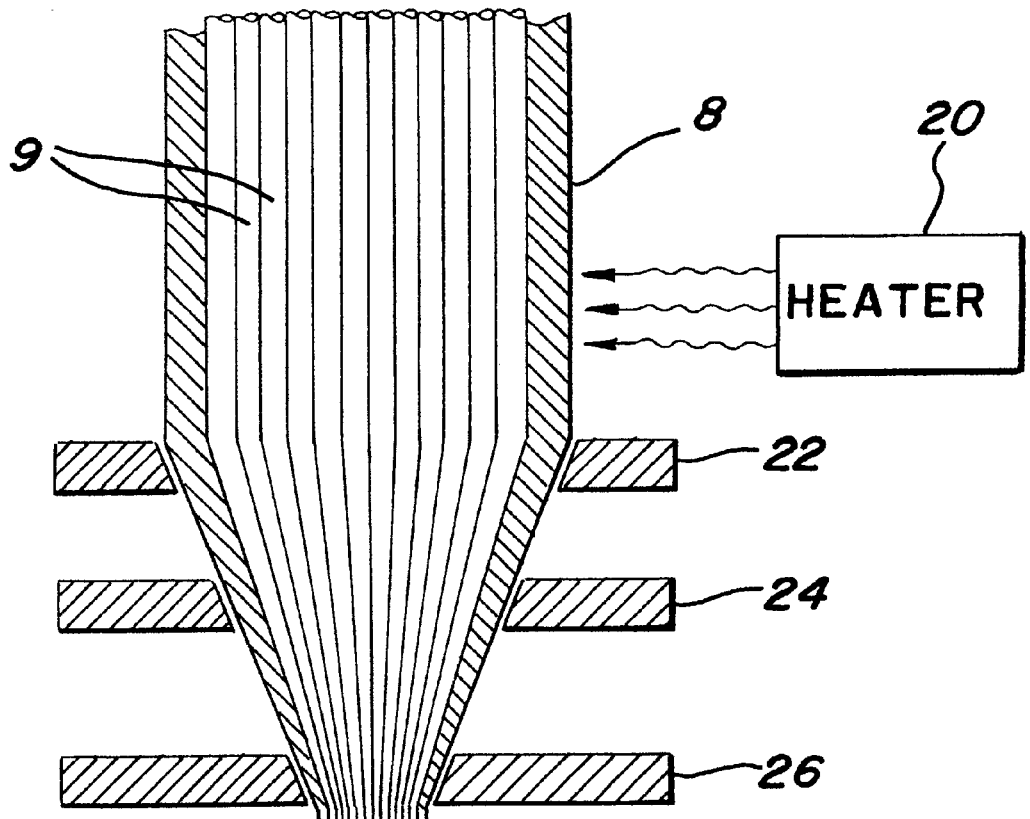
FIG. 2A is a schematic view of the process of reducing an outer glass housing and bundled capillary tubes.
Figure 2B:
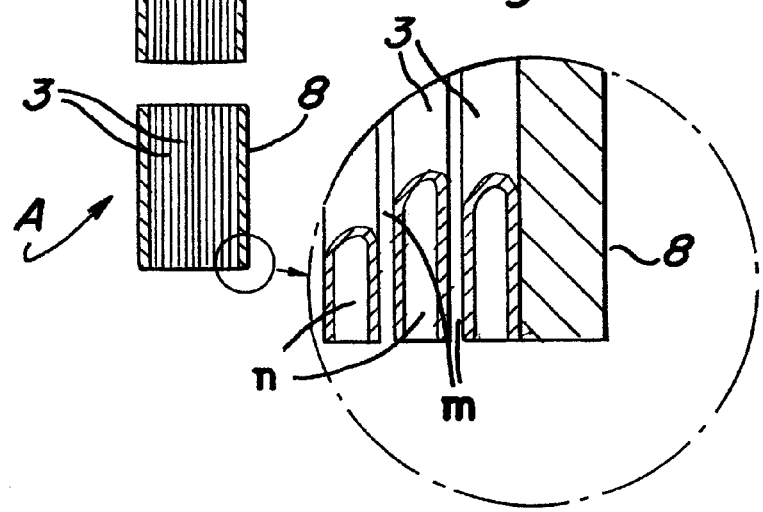
FIG. 2B is a magnified cross sectional view of one edge of the composite glass tube and bundled capillary tubes.
Figure 4:
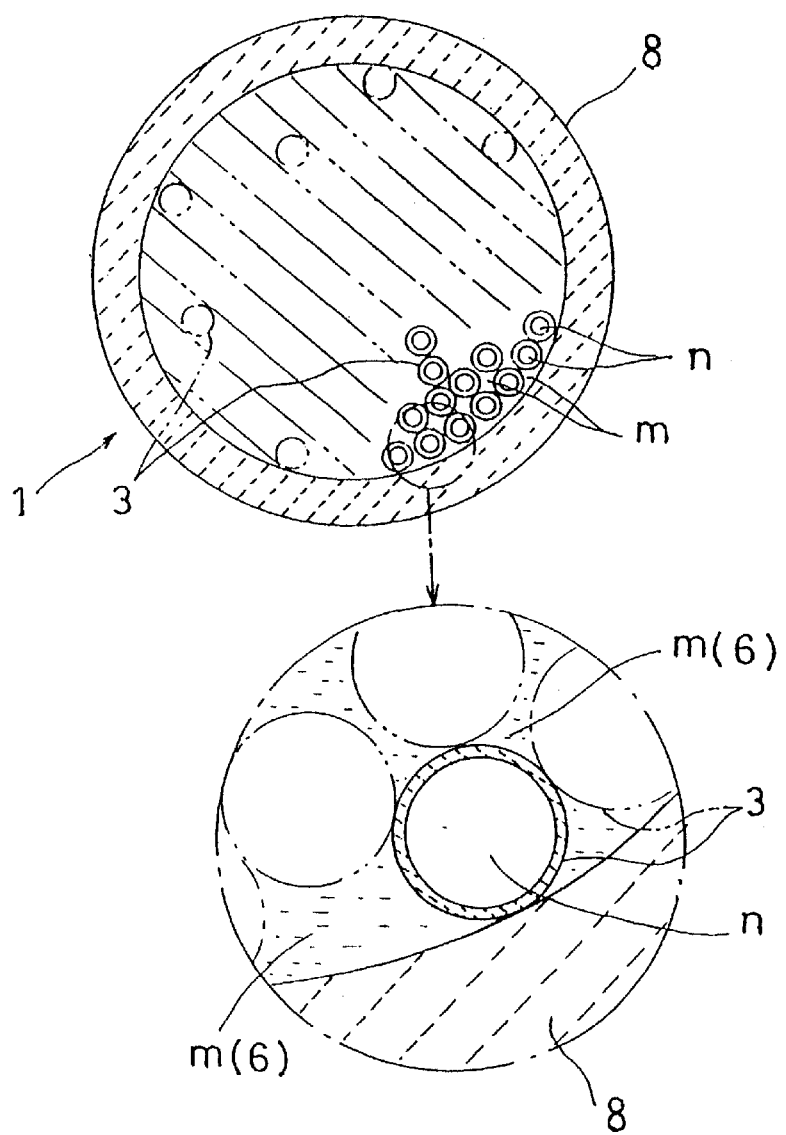
FIG. 4 is a cross sectional schematic view of the bundled capillary tubes and outer glass tube and is a magnified edge section disclosing the passageway and gaps.

Referring to FIG. 2A, a plurality of capillary tubes 9, for example, from scores to hundreds of tubes of $SiO_2$—$Li_2O$ glass can be aligned in a parallel manner within an outer housing glass tube 8, such as a borosilicate glass that is acid soluble in about 1 mol/liter of HCl or $HNO_3$, for example, $SiO_2$—$B_2O_3$—$Na_2O$ glass to thereby provide an acid soluble tubular glass member 8. The resultant intermediate composite of the outer glass tube 8 and the bundle of capillary tubes 9 can then be appropriately heated by a heater 20 to a temperature of approximately 650° C. to 700° C., and then the composite can be drawn through a series of dies 22, 24, 26 to reduce the diameter of the composite, so that the individual capillary tubes 3 will have a thin wall thickness of about 10 microns with penetration holes m, or passageways of, approximately 10 to 100 microns in diameter. This composite is then diced or cut to a specific length, depending upon the particular application of the ion concentration measuring electrode, for example, 1 to 10 cm. Referring to FIG. 2B, the area of gaps m between the capillary tubes 3 are smaller then the passageways n.

Referring to FIG. 3A, the composite, or diced length of bundled tubing, is masked so that the outer glass tube 8 is covered with an acid resistant heat shrink tube 10 while exposing both ends 8A of the acid soluble glass tube 8. This composite is then emerged in one mol/liter of acid, such as HCL and $HNO_3$ so that the ends 8a of the glass tube 8 are dissolved, thereby exposing ends and partial sides of the capillary tubes 3.

As shown in FIG. 3B, one exposed end side of the capillary tubes 3 is molded in a thermoplastic resin 11, in such a manner that the molding resin 11 penetrates deeper into the respective gaps m, that are on the exterior sides of the capillary tubes due to the capillary phenomenon, while the molding resin will not penetrate as far into the passageway or penetration holes n of the individual capillary tubes 3. Various types of resin can be used such as silicone resin, epoxy resin, polyvinyl chloride (PVC), urethane resin, urethane rubber and cyano acrylate resin. With the composite structure thereby capped at one end, the composite structure is then placed into a vacuum housing 16, as shown in FIG. 3C. The composite is then immersed in an internal solution 6, such as in a gel, slurry or liquid form, so that the vacuum will draw the internal solution 6 into the gaps m between the capillaries 3. It will also be injected into the capillary tubes or passageways n which can then be removed in a later process.

As shown in FIG. 3D, an internal electrode 5 to which a lead wire 4 is connected can be inserted from the other end side of the capillary tubes 3 into a gap m between the exterior surfaces of the capillary tubes. The lead wire 4 can be folded outward at the end portion of the glass tube and the other end side of the capillary tubes 3 can then be molded also in the thermoplastic resin 11, so as to hold the lead wire in a liquid-type manner.

When applying the sealing molding material of the thermoplastic resin 11, it is important that the resin 11 penetrates into the gaps and between the capillary tubes so that both end sides of the gap that are filled with the internal solution 6 will be sealed by the resin 11 with the internal solution 6 filling up the remainder of the gap m. Referring to FIG. 3E, the electrode lead wire 4 is shown as sealed by the resin 11. The end of the resin material is cut off, as shown in FIG. 3F, thereby leaving the sealing material only in the gaps m at both end sides of the composite. As shown in FIG. 3F, the cut line is indicated by the virtual line j, at both end sides of the capillary tubes 3 and, as a result, any internal solution 6 which may be within the penetration or passageway holes n of the capillary tubes 3 can be discharged. As a result of this manufacturing process, a composite glass electrode body member 1 of a flow through type, in which an internal solution 6 has an extended surface area as a result of its positions within the gaps n, is provided. The internal electrode 5 is immersed within the internal solution which in turn is sealed about the outer exterior surfaces of the bundled capillary tubes 3.

Figure 5:
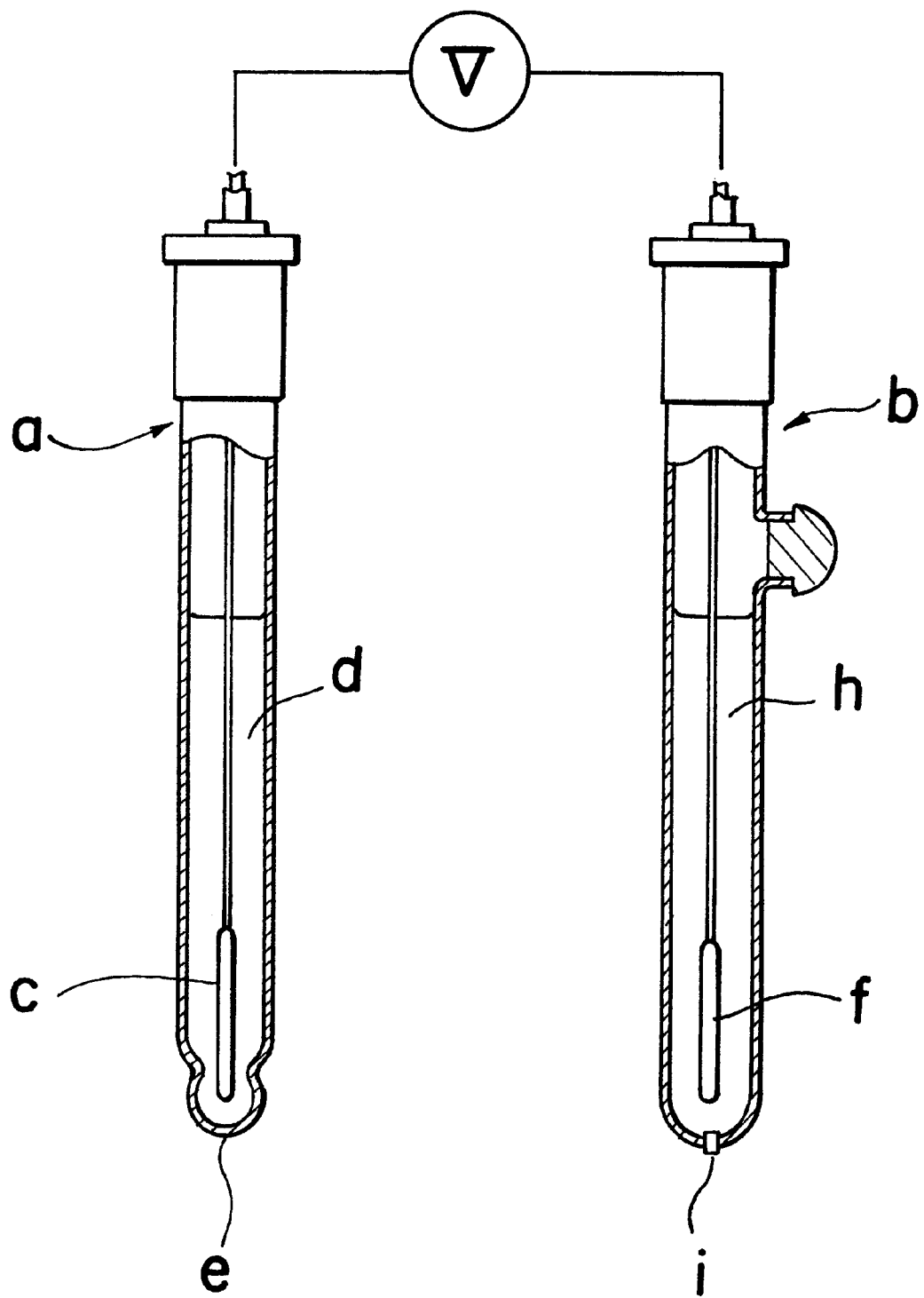
FIG. 5 is an explanatory schematic view of a conventional pH meter composed of a glass electrode and a reference electrode.

In such a construction of the glass electrode 1, the passageway walls n of the capillary tubes 3 form the electrode response section and since a large number of capillary tubes 3 are bundled, the liquid contact area is considerably wider in the electrode response section shown than, for example, in the conventional reference electrode of FIG. 5. As a result of this design, the impedance of the electrode response section can be lowered substantially and since the capillary tubes have a very thin wall, the response performance can be dramatically enhanced while maintaining an additional strength and durability in view of the bundled configuration within the outer housing of the glass tube 8.

As an alternative processing step of forming the glass electrode 1, it is possible to mold with the thermoplastic resin 11, one end side the gaps m of the capillary tubes 3, and then subsequently pour the internal solution 6 into the gaps, insert the internal electrode 5 into the gaps m and mold the other end side of the capillary 3 in resin. The resulting molding resin 11 on the other side can then be cut away to expose the passageway holes n. Additionally, by inserting a plurality of capillary tubes 9 into the acid soluble glass tube 8, redrawing them and then dicing them to a specific length, the electrode material A is prepared. Alternatively, by bundling a plurality of capillary tubes 3 into a specific shape with a heat shrink tube as the outer tubular member, and then dicing them, both end sides of the heat shrink tube may be cut off to form the electrode material A, or alternatively, without cutting off the both end sides of the tube, a cut may be formed at one end side of the tubes and the lead wire 4 connected to an internal electrode 5 may be folded outward from this cut. Additionally, as another alternative method of manufacturing a plurality of capillary tubes within a heat shrink outer tube, it is possible to set the end portion of the heat shrink tube slightly inside of the end portion of the capillary tubes 3 and therefore it would not be necessary to cut off both the end sides of the tubes, or to have a process step for cutting, and the lead wire 4 can be connected to an internal electrode 5 and can be folded outward. The heat shrinked plastic tubing can be polyolefine, silicone resin and PVC.

Referring to FIG. 1, an ion concentration measuring instrument, such as a pH meter of a flow through type, is shown. The glass electrode body member 1 of this construction has been described and sample fluid will flow through the passageways n of the capillary tubes 3. The measurement can be made by the internal electrode 5. Downstream of the glass electrode 1, is a liquid junction r which is formed in the conduit 7 to communicate with a reference electrode internal solution 13 which surrounds the conduit 7. A glass-made reference electrode body or housing 12 can be kept in a fluid-type contact with the conduit 7 and a reference electrode internal electrode (Ag/AgCl) 15 can be immersed in the reference electrode internal solution 13, with a lead out electrode wire 14 being connected to the reference electrode body 12. As a result of the measurements of the reference electrode 2 and the glass electrode 1, a calculation can be made of the pH of the sample fluid in a manner known in the art. As can be appreciated, both the reference electrode b shown in FIG. 5 and the glass electrode 1 of the invention could be combined together as an alternative embodiment and it is quite possible to measure, other than pH, various ions, such as $Na^+$.

As a result of the ion concentration measuring electrode of the present invention, an extremely wide liquid contact area is formed as a result of bundling a plurality of capillary tubes to create an enlarged electrode response section. As a result of this configuration, the impedance of the electrode response section can be lowered and it is not necessary to use a high input insulated circuit, while the capillary tubes themselves can be formed of relatively thin walls, so that the response performance can be dramatically enhanced, while strength can be maintained due to the bundled configuration.

In summary, an ion concentration electrode unit having an electrode response section of low impedance with high response performance can be provided while eliminating the requirement of a high input insulating circuit. The advantages of the present invention is achieved by bundling a plurality of capillary tubes and sealing both ends of the bundled tubes so that the gaps between the exterior surfaces of the tubes can maintain an internal solution and be in communication with an internal electrode connected to a lead wire. The passageways in the tubes provide an increased flow area for the sample fluid. This liquid contact area of the electrode response section is thereby markedly increased over that of the prior art electrode response sections and hence the impedance is substantially lowered. For example, it can be set to be at least 100th, or less, of the conventional level. As can be appreciated, the ion concentration can be measured by an mV meter, for example a digital volt meter. This configuration also lends itself to miniaturization for small hand-held instrumentation. Since the capillary tubes can be formed of a very thin wall diameter, the response performance is enhanced dramatically, while the structural strength is adequately maintained.

In the production process, the ion concentration measuring unit can be manufactured by initially bundling a plurality of capillary tubes, in parallel alignment, inside of an exterior acid soluble glass tube. In the production process, a length of the bundled capillary tubes and exterior tube can be heated to a temperature whereby they can be drawn through a series of dies to reduce the composite diameter of the structure. Diced sections of this composite tubing can be cut to appropriate predetermined lengths and then processed in a manner to seal the gaps between the exterior surfaces of the capillary tubes, so that an internal solution and an internal electrode can be mounted. The passageways of the capillary tubes are processed to be open to provide the increased flow area surface for the sample fluid.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. An ion concentration measuring electrode unit, comprising:
   a body member having a plurality of hollow tubes extending through the body member to provide a plurality of passageways for a sample to be tested and an internal solution complimentarily to the ion to be measured surrounds and contacts exterior surfaces of the hollow tubes; and
   an internal electrode is immersed within the internal solution whereby a large internal surface area is provided by the plurality of the passageways for interfacing with the internal solution on the exterior surfaces of the hollow tubes to enable a reduced impedance in measurement of the sample.

2. The electrode unit of claim 1 wherein the hollow tubes are glass capillaries of $SiO_2$—$Li_2O$.

3. The electrode unit of claim 1 wherein a wall thickness of the hollow tubes is about 10 microns.

4. The electrode unit of claim 1 wherein an internal diameter of the hollow tube is approximately in the range of 10 to 100 microns.

5. The electrode unit of claim 1 wherein the hollow tubes are bundled to maximize a flow path through the passageways.

6. The electrode unit of claim 5 wherein the hollow tubes have a wall thickness of about 10 microns and internal diameter of approximately 10 to 100 microns.

7. The electrode unit of claim 5 wherein the hollow tubes are mounted in an outer housing tube and gaps between the exterior surface of the hollow tubes are sealed at a first end of the body member and at a second end of the body member to retain the internal solution.

8. The electrode unit of claim 7 wherein the internal solution is KCl.

9. The electrode unit of claim 7 wherein the hollow tubes are glass capillaries of $SiO_2$—$Li_2O$.

10. The electrode unit of claim 7 wherein the gaps are sealed with a moulding resin.

11. An ion concentration meter assembly comprising:

a sample flow conduit;

a body member positioned in the conduit and having a plurality of hollow tubes extending through the body member to provide a plurality of passageways for a sample to be tested and an internal solution complimentarily to the ion to be measured surrounds and contacts exterior surfaces of the hollow tubes;

an internal electrode is immersed within the internal solution whereby a large internal surface area is provided by the plurality of the passageways for interfacing with the internal solution on the exterior surfaces of the hollow tubes to enable a reduced impedance in measurement of the sample;

a liquid junction connected to the conduit;

a reference electrode unit connected to the liquid junction and having a reference electrode in a reference fluid; and means for receiving outputs of the internal electrode and the reference electrode to measure an ion concentration.

12. The electrode unit of claim 11 wherein the hollow tubes are glass capillaries of $SiO_2$—$Li_2O$.

13. The electrode unit of claim 11 wherein a wall thickness of the hollow tubes is about 10 microns.

14. The electrode unit of claim 11 wherein an internal diameter of the hollow tube is approximately in the range of 10 to 100 microns.

15. The electrode unit of claim 11 wherein the hollow tubes are mounted in an outer housing tube and gaps between the exterior surface of the hollow tubes are sealed at a first end of the body member and at a second end of the body member to retain the internal solution.

16. A method of manufacturing an ion concentration measuring electrode unit comprising the steps of:

securing a plurality of capillary tubes together to provide a plurality of passageways for a sample fluid;

inserting an internal solution into the area between exterior surfaces of the capillary tubes;

positioning an internal electrode in the internal solution; and sealing the internal solution so that the sample fluid will pass through the passageways whereby a large internal surface area is provided by the passageways for interfacing with the internal solution on the exterior surfaces of the capillary tubes to enable a reduced impedance in measurement of the sample fluid.

17. The method of claim 16 wherein the step of securing includes providing an outer glass tube and the capillary tubes are made of $SiO_2$—$Li_2O$ and heating and drawing the outer glass tube and plurality of capillary tubes to provide internal diameters of the capillary tubes in the approximate range of 10 to 100 microns.

18. The method of claim 16 wherein the steps of sealing include providing a sealing material on the respective ends of the capillary tubes.

19. The method of claim 18 wherein the sealing material is drawn by a capillary action into spaces between the capillary tubes.

20. The method of claim 16 wherein the step of inserting the internal solution includes sealing one end of the capillary tubes and each space between the capillary tubes and drawing the internal solution into the spaces between the capillary tubes.

* * * * *